United States Patent [19]

Schromm et al.

[11] Patent Number: 5,223,614

[45] Date of Patent: Jun. 29, 1993

[54] NEW QUATERNARY AMMONIUM COMPOUNDS, THEIR PREPARATION AND USE

[75] Inventors: Kurt Schromm, Ingleheim am Rhein; Anton Mentrup, Wiesbaden; Ernst-Otto Renth; Gojko Mualcevic, both of Ingleheim am Rhein; Werner Traunecker, Munster-Sarmsheim, all of Fed. Rep. of Germany

[73] Assignee: Boehringer Ingelheim GmbH, Ingleheim am Rhein, Fed. Rep. of Germany

[21] Appl. No.: 603,585

[22] Filed: Oct. 25, 1990

Related U.S. Application Data

[63] Continuation of Ser. No. 286,442, Dec. 19, 1988, abandoned.

[30] Foreign Application Priority Data

Dec. 19, 1987 [DE] Fed. Rep. of Germany ....... 3743265

[51] Int. Cl.$^5$ .......................................... C07D 265/36
[52] U.S. Cl. .................................... 544/105; 546/184; 546/221; 548/215; 548/221; 564/281; 564/282; 564/291; 568/705

[58] Field of Search ............... 564/283, 281, 282, 291; 544/105; 546/184, 221; 548/215, 221; 574/230.5, 299, 330, 375; 568/705

[56] References Cited

U.S. PATENT DOCUMENTS 4,599,335 7/1986 Rentzea et al. .................... 564/282

OTHER PUBLICATIONS

Chemcial Abstracts, vol. 101, p. 772, 191939z, 1984.
Chemical Abstracts, vol. 80, p. 274, No. 7, 36875e, 1974.

*Primary Examiner*—José G. Dees
*Assistant Examiner*—Deborah D. Carr
*Attorney, Agent, or Firm*—D. E. Frankhouser; A. R. Stempel; M-E. M. Timbers

[57] ABSTRACT

Compounds of formula

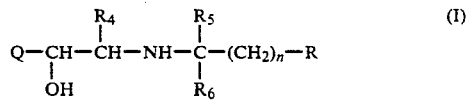

wherein the substituents are defined hereinbelow, useful in the treatment of bronchospasm are described.

5 Claims, No Drawings

NEW QUATERNARY AMMONIUM COMPOUNDS, THEIR PREPARATION AND USE

This is a continuation, of application Ser. No. 286,442, filed Dec. 19, 1988, now abandoned.

The invention relates to quaternary ammonium compounds, and the preparation and use thereof. The compounds of the invention may be prepared by methods known per se and used as pharmaceuticals, particularly for inhalation.

We have found that the introduction of a quaternary ammonium group at a suitable point in the molecules of known broncholytically active compounds which are effective when inhaled makes it possible to eliminate unwanted systemic side effects to a great extent whilst substantially retaining the broncholytic (topical) effect. We have found that the nature of the quaternary ammonium grouping may be selected from a wide range of variations without crucially affecting the differentiation between desirable and undesirable effects according to the invention.

According to the invention, we provide compounds of formula I

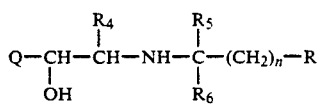

(I)

wherein

Q represents a substituted phenyl group;

R represents a group, such as an alkoxy, arylalkoxy, aryloxyalkoxy, aryl, aryloxy arylcarbonamido group, a heterocyclic group or a heterocyclically substituted carbonamido group, which includes also a quaternary ammonium grouping;

$R_4$ represents H, $CH_3$ or $C_2H_5$;

$R_5$ represents H or $CH_3$;

$R_6$ represents H or $CH_3$;

n represents an integer selected from 1, 2, 3, 4 and 5.

The compounds of the invention may in one preferred embodiment be represented essentially by the formula Ia

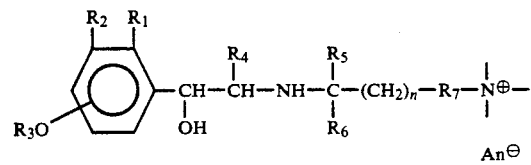

(Ia)

in which, unless otherwise stated, n represents an integer selected from 1, 2, 3, 4 and 5;

$R_1$ represents H, $CH_3$, $OCH_3$, Cl, or F;

$R_2$ represents H, $R_3O$—, —$CH_2OH$, —NHCHO, —NHCOCH$_3$, —NHSO$_2$CH$_3$, or —NHCONH$_2$;

$R_3$ represents H, acyl, or N,N-dialkylcarbamoyl, the groups $R_3O$ being in the 4- or 5- positions;

the group II

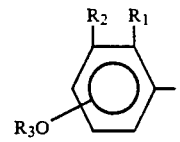

(II)

may also represent one of the groups

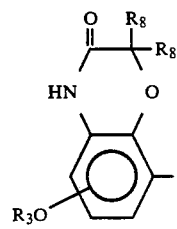

(IIa)

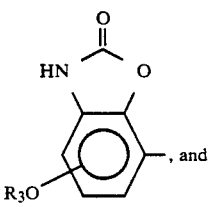

(IIb)

, and

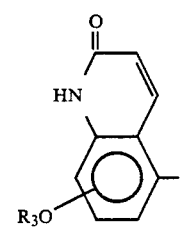

(IIc)

wherein $R_3$ is as hereinbefore defined and $R_8$ represents H or $CH_3$;

$R_4$ represents H, $CH_3$, or $C_2H_5$;

$R_5$ represents H or $CH_3$;

$R_6$ represents H or $CH_3$;

$R_7$ represents a single bond or a divalent bridging member which may also be bound to the ammonium nitrogen via ring atoms of a heterocyclic group;

represents a quaternary ammonium group;

$An^\ominus$ represents an anion.

In a further preferred embodiment, the grouping

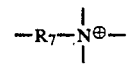

primarily represents one of the groups

| | |
|---|---|
| —E, | (III a) |
| —Ar—B—E, | (III b) |
| —O—Ar—B—E, | (III c) |
| —NH—CO—E, | (III d) |
| —NH—CO—Ar—B—E, | (III e) |
| —O—($C_mH_{2m}$)—A—E, | (III f) |

-continued

—O—$(C_mH_{2m})$—A—Ar—B—E,  (III g)

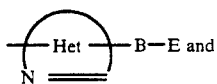  (III h)

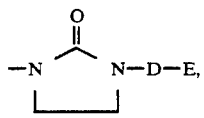  (III i)

n and $R_1$ to $R_6$ being as defined hereinbefore.

In the above definitions of (IIIa) to (IIIi),
m represents an integer selected from 2, 3, 4, 5 and 6;

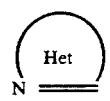

represents a nitrogen heterocycle which may be condensed with a benzene ring and which may be substituted or unsubstituted and may optionally contain one or more additional heteroatoms in the ring;

Ar represents arylene, preferably unsubstituted or substituted phenylene or naphthylene;

A represents a single bond or a NH—CO—$(C_{1-4})$-alkylene group;

B represents a single bond or an —O—$(C_{1-4})$-alkylene, —NH—CO—$(C_{1-4})$-alkylene, or —$(C_{1-4})$-alkylene group;

D represents a —$(C_{1-4})$-alkylene group; and

E represents one of the groups

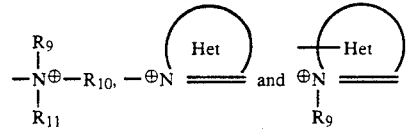

(in which $R_9$ represents a $(C_{1-4})$-alkyl group;

$R_{10}$ represents a $(C_{1-4})$-alkyl group; or $R_9$ and $R_{10}$ together represent a $(C_{4-6})$-alkylene group; and $R_{11}$ represents a $(C_{1-4})$-alkyl, $(C_{1-4})$-alkylene-COO$^\ominus$, $(C_{1-4})$-alkylene-SO$_3^\ominus$, $(C_{1-4})$-alkylene-OH, or $(C_{3-6})$-cycloalkyl group; and the group

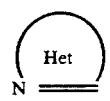

is as defined above).

Typical examples of E include
—N$^\oplus$(CH$_3$)$_3$,
—N$^\oplus$(CH$_3$)$_2$CH$_2$CH$_2$CH$_2$SO$_3^\ominus$,
—N$^\oplus$(CH$_3$)$_2$—(CH$_2$)$_4$—SO$_3^\ominus$,
—N$^\oplus$(CH$_3$)$_2$CH$_2$CH$_2$CO$_2^\ominus$,

-continued

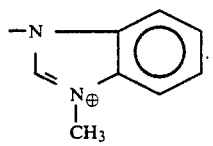

Particular mention should be made of the following preferred definitions for the grouping

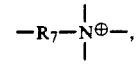

in which the groupings and groups are as defined above:

—N$^\oplus$R$_9$R$_{10}$R$_{11}$  (III a 1)

  (III a 2)

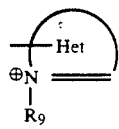  (III a 3)

—Ar—B—N$^\oplus$R$_9$R$_{10}$R$_{11}$  (III b 1)

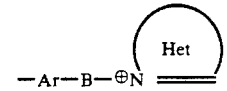  (III b 2)

—O—Ar—B—N$^\oplus$R$_9$R$_{10}$R$_{11}$  (III c 1)

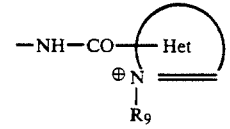  (III d 1)

—NH—CO—Ar—B—N$^\oplus$R$_9$R$_{10}$R$_{11}$  (III e 1)
—O—$(C_mH_{2m})$—A—N$^\oplus$R$_9$R$_{10}$R$_{11}$  (III f 1)
—O—$(C_mH_{2m})$—A—Ar—B—N$^\oplus$R$_9$R$_{10}$R$_{11}$  (III g 1)

  (III h 1)

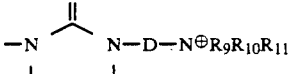  (III i)

The alkyl and alkylene groups in the above definitions may be straight-chained or branched. Unless otherwise stated, they contain 1 to 6, preferably 1 to 4, and most particularly 1 or 2 carbon atoms. This also applies to the carbon chains which are components of other groups. Examples of substituents in aryl(ene) include, in particular, F, Cl, CH$_3$ and CH$_3$O groups. The terms "aryl" and "arylene" refer to the appropriate groups derived from benzene or naphthalene. "Acyl groups" in this case denote carboxylic acid groups with up to 7 carbon atoms, particularly acetyl. The bridge $R_7$ may be linked to the nitrogen atom of the quaternary ammonium group. Alternatively, if the quaternary ammonium group is part of a heterocyclic group, the bridge may be connected to another ring atom of the heterocyclic group. Groups falling into this latter category include in particular

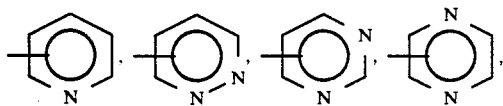

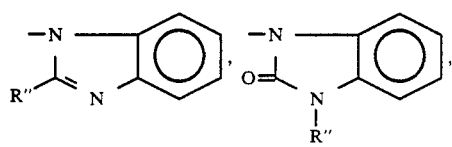

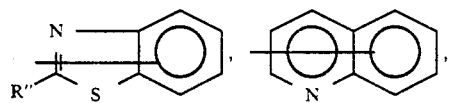

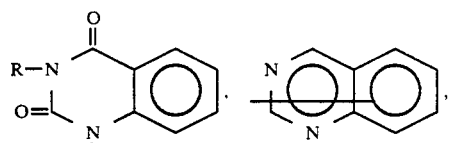

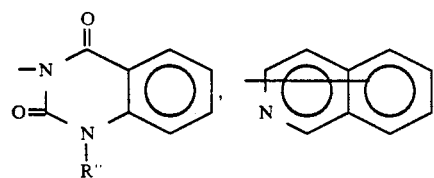

(in which $R^{11}$ represents H or $C_{1-4}$-alkyl), and triazines.

In a further preferred embodiment of the invention
$R_1$ represents H, $CH_3$, $OCH_3$, Cl or F;
$R_2$ represents OH or, when $R_1$ equals Cl or F, $R_2$ may also represent H; or
$R_1$ and $R_2$ together may also represent

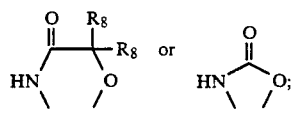

(in which $R_8$ is as hereinbefore defined)
$R_3$ represents a hydrogen atom;
$R_4$ represents H or $C_2H_5$;
$R_5$ and $R_6$ both represent H or both represent $CH_3$;
n represents an integer selected from 1, 2 and 3;
$R_7$

represents a group

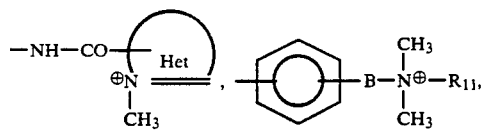

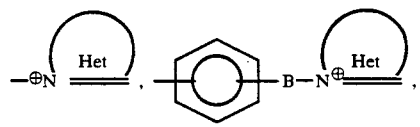

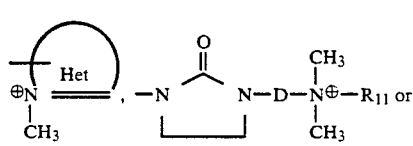

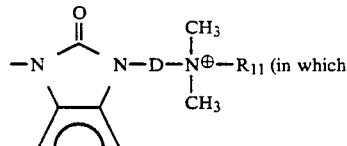

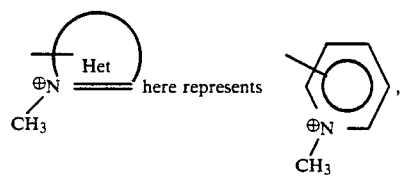

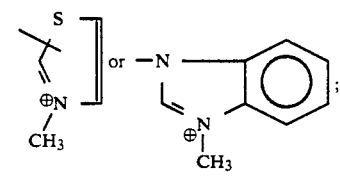

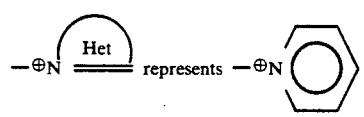

whilst B, D and $R_{11}$ are as hereinbefore defined).

Particular mention should be made of the compounds in which the following combinations of substituents occur:

(a) $R_1$ represents a methyl or methoxy group, $R_2$ represents a hydroxyl group, and $R_3$ represents a 4-hydroxyl group;

(b) $R_1$ represents a hydrogen atom, $R_2$ represents a hydroxyl group, and $R_3$ represents a 4- or 5-hydroxyl group;

(c) $R_1$ and $R_2$ together represent

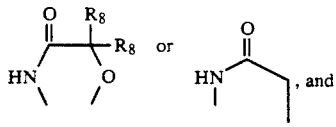

$R_3$ represents a 4- or 5-hydroxyl group;
$R_4$ represents a hydrogen atom, if $R_5$ and $R_6$ represent methyl groups, but $C_2H_5$, if $R_5$ and $R_6$ represent H;

$$R_7-\overset{|}{\underset{|}{N^\oplus}}-$$

represents

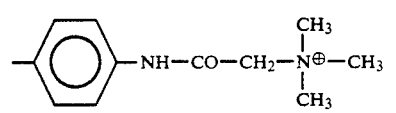

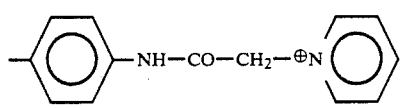

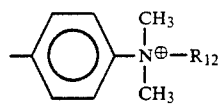

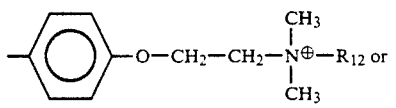

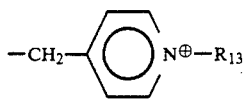

(in which $R_{12}$ and $R_{13}$ represent $CH_3$, $CH_2-COO^\ominus$, $CH_2-CH_2-COO^\ominus$ or $CH_2-CH_2-CH_2-SO_3^\ominus$).

The compounds according to the invention may occur as mixtures of enantiomers, particularly as racemates, and optionally either as pairs of diastereoisomers or as pure enantiomers, and as salts with (preferably physiologically acceptable) acids, and the invention extends to all such forms of the compounds of formula I.

The compounds of the invention may be prepared by a variety of methods.

Accordingly, in a further aspect of the invention, we provide a process for preparing compounds of formula I as described above, wherein a) a compound of formula IV

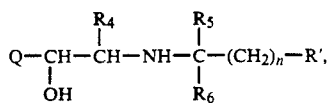

wherein n, Q, $R_4$, $R_5$ and $R_6$ are as defined above, R' is a tertiary amino group which corresponds at least in part to the quaternary ammonium group-containing group R, or a protected form thereof in which any hydroxyl group or amino group it is desired to protect is protected by hydrogenolytically-removable protecting groups, is reacted with an alkylating agent, and any protecting groups present are removed by hydrogenolysis;
or b) if it is desired to prepare a compound of formula VII

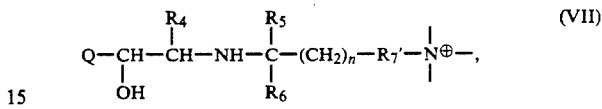

wherein n, $R_4$, $R_5$, $R_6$ and Q are as defined above and $R_7'$ represents a group $R_7$ which is bound to the quaternary ammonium nitrogen via an aliphatic carbon atom, a compound of formula VIII

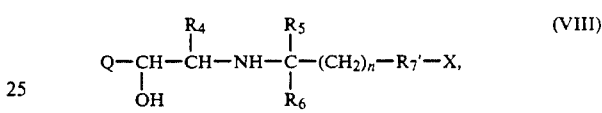

(wherein the symbols are all defined as above and X represents a leaving group is reacted with a tertiary amine

to provide the desired quaternary ammonium compound, followed, if desired, by separation of any mixture of enantiomers into pure enantiomeric forms or other enantiomeric mixtures, and formation of any desired acid addition salts.

Process (a) above is suitable for preparing compounds of formula I in which the quaternary ammonium group is not in the form

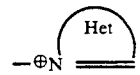

Compounds selected from $Cl-(C_{1-4})$-alkylene-$SO_3Na$ and $HO-(C_{1-4})$-alkylene-$SO_2-O-(C_{1-4})$-alkylene-$SO_3Na$ are particularly suitable for the introduction of a $(C_{1-4})$-alkylene-$SO_3^\ominus$ group.

The reaction is expediently carried out in an inert polar solvent at ambient temperature or at an elevated temperature up to about 100° C.

The starting materials of formula IV may be obtained by methods known per se. Thus, aminoketones of formula V

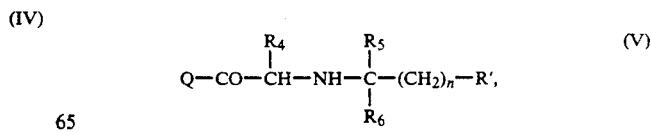

wherein Q, $R^4$, $R^5$, $R^6$, $R^1$ and n are as defined above, or Schiff base of the formula VI

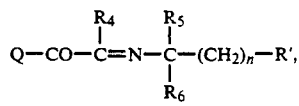

(wherein the symbols are defined as hereinbefore) may be converted into compounds of formula IV by reduction with hydrogen in the presence of hydrogenation catalysts such as palladium, platinum or Raney nickel, or by reaction with hydrides such as sodium hydride in suitable solvents such as ethanol. Any protecting groups present may if necessary or desired be removed in the usual way.

In process (b) above, the leaving group X is preferably a chlorine, bromine or iodine atom or an alkyl- or arylsulphonic acid group.

The reaction is preferably effected in a protic or aprotic solvent such as methanol or dimethylformamide at temperatures of between ambient temperature and about 100° C.

Any hydrogenolytically-cleavable protecting groups present may be removed after the reaction if necessary or desired by conventional methods.

The starting compounds of formula VIII may be prepared, for example, from aminoketones of formula IX

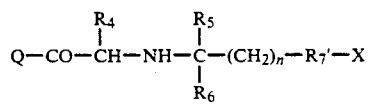

by reaction thereof with a hydride such as sodium hydride or diborane.

The compounds of formula IX may in turn be obtained by methods known per se.

Any protecting groups present which it is desired to remove may expediently be removed by hydrogenolysis with palladium as catalyst in an inert solvent.

The compounds according to the invention always will contain at least one asymmetric carbon atom. In order to obtain compounds of formula I in the form of specific enantiomers or (in the case of several centres of asymmetry) diastereoisomeric pairs of antipodes, it is convenient to use starting materials, e.g. of formula IV or X, in which the desired configuration is already present at the centres of asymmetry in question.

The compounds according to the invention may if desired by converted in a manner known per se into salts. For pharmaceutical use these will preferably be formed with physiologically acceptable acids, and these may be either organic or inorganic.

Suitable acids for salt formation include, for example, inorganic acids such as hydrochloric, hydrobromic, sulphuric and phosphoric acids, and organic acids such as methylsulphuric, tartaric, fumaric, citric, maleic, succunic, gluconic, malic, p-toluenesulphonic, methanesulphonic and amidosulphonic acids.

The compounds of the invention are suitable for use in pharmaceutical compositions. In particular they have broncholytic, spasmolytic and anti-allergic activity, they increase ciliary activity and reduce inflammatory/exudative reactions. They may therefore be used inter alia for treating all types of asthma and bronchitis.

The dosage for therapeutic and prophylactic use will in general depend on the nature and gravity of the illness in question.

For adults, the dosage for the preferred route of administration, namely inhalation, is preferably from 0.001 to 0.5 mg per day. The preparations are obtained in conventional manner using normal diluents, excipients and/or carriers. The compounds according to the invention may also be combined with other active substances, e.g. parasympatholytics (e.g. ipratropium bromide, oxytropium bromide), secretolytics (e.g. bromhexine, ambroxol), antibiotics (e.g. doxycycline), corticosteroids (e.g. beclomethasone dipropionate, flunisolide, budesonide) or other anti-asthma preparations such as disodium cromoglycate, nedocromil and anti-allergic substances.

The following non-limiting examples illustrate formulations which incorporate the compounds of the invention:

1. Powder for inhalation

Micronised powdered active substance (compound of formula I; particle size about 0.5 to 7 microns) is packed into hard gelatine capsules in quantities of 0.02 mg with 10 mg of micronised lactose and, optionally, suitable quantities of other active substances. The powder is inhaled from conventional inhaling devices, e.g. according to DE-A-3345722.

2. Metering aerosol

| | |
|---|---|
| Active substance according to Example 8 hereinbelow | 0.1% by weight |
| Sorbitane trioleate | 0.5% by weight |
| Monofluorotrichloromethane and difluorodichloromethane (2:3) | 99.4% by weight |

The mixture is packed into metering aerosols of suitable type. The metering device is designed, for example, so as to release 0.05 ml of the preparation on each actuation.

The advantage of the compounds according to the invention is that, when they are inhaled, by comparison with known bronchospasmolytic $\beta$-mimetics, they show a particularly marked selectivity in the relationship between bronchospasmolysis and increased heart rate, positive inotropic effects and tremor. The broncholytic activity is achieved with low doses and the activity is long-lasting.

Some pharmacological activity data for compounds according to the invention are given hereinafter.

The $EC_{50}$ by inhalation was determined on conscious, fasting guinea-pigs according to Kallos P. and Pagel, W. (Acta med. scand. 91, 292 (1937)) (histamine spasm). The substances were tested in the form of an aqueous solution.

| $EC_{50}$ | % |
|---|---|
| A | 0.06 |
| B | 0.06 |
| C | 0.09 |
| D | 0.06 |
| E | 0.5 |
| F | 0.3 |
| G | 0.02 |
| H | 0.05 |
| I | 0.02 |
| J | 0.004 |

11
-continued

| EC$_{50}$ | % |
|---|---|

| | K | 0.02 |
|---|---|---|

Compounds tested

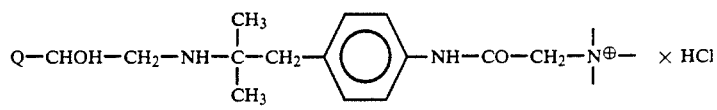

| Compound | Q | $-\overset{|}{\underset{|}{N}}^{\oplus}-$ |
|---|---|---|
| A: | ![structure] 2-(acetyl)-3-hydroxy-phenol ether with HN | $-N^{\oplus}(CH_3)_3 Cl^{\ominus}$ |
| B: | same phenol-acetyl-ether | $-^{\oplus}N$-pyridinium $Cl^{\ominus}$ |
| C: | 2,3-dihydroxy-methylphenyl (OH, CH$_3$, HO) | $-N^{\oplus}(CH_3)_3 Cl^{\ominus}$ |
| D: | HN-C(=O)-O benzoxazolone with HO | $-^{\oplus}N(CH_3)_3 Cl^{\ominus}$ |
| E: | 3,5-dihydroxyphenyl (OH, OH) | $-^{\oplus}N(CH_3)_3 Cl^{\ominus}$ |

Compounds of formula

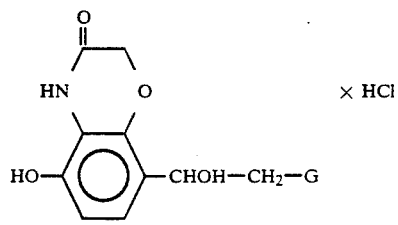  × HCl

| Compound | G |
|---|---|

-continued

F: 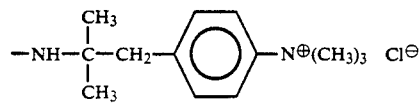

G: 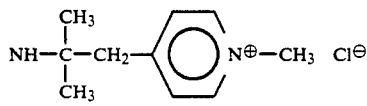

H: 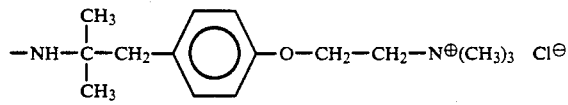

I: 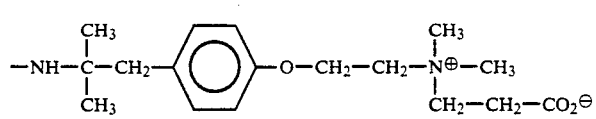

J: 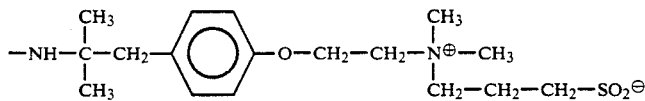

K: 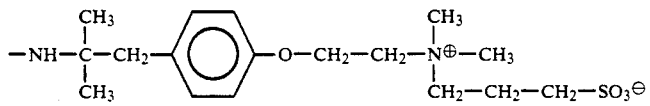

The following non-limiting examples illustrate processes whereby the compounds of the invention may be synthesised.

EXAMPLE 1

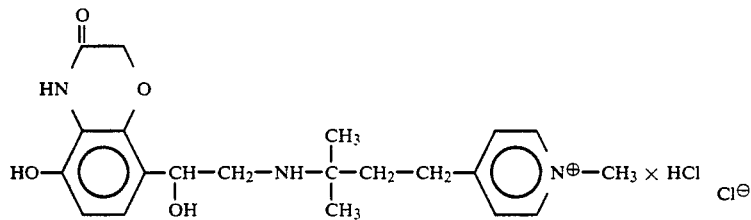

1.9 g of 5'-hydroxy-8'-[1-hydroxy-2-[4-(4-pyridyl)-2-methyl-2-butylamino]-ethyl]-2H-1,4-benzoxazin-3-(4H)-one-monohydrochloride are dissolved in a mixture of 3 ml of dimethylformamide and 1 ml of water and 1.27 g of methyliodide are added. After 12 hours the solution is mixed with 5 ml of alcohol, acidified with conc. HCl and diluted with acetone; the crystals precipitated are suction filtered after about 1 hour and 1.2 g of the compound are obtained by precipitation with water, conc. hydrochloric acid and alcohol.

M.p. 207°–209° C. 56% of theory.

The starting compound may be prepared by the following method:

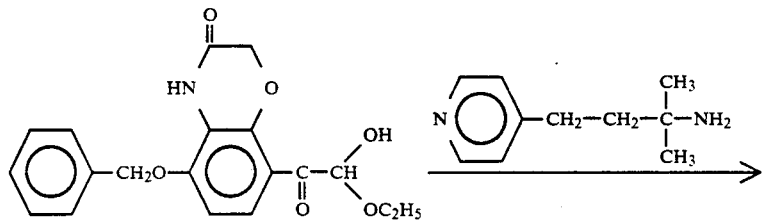

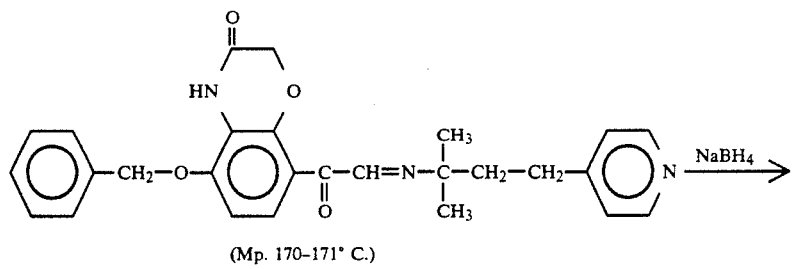

(Mp. 170–171° C.)

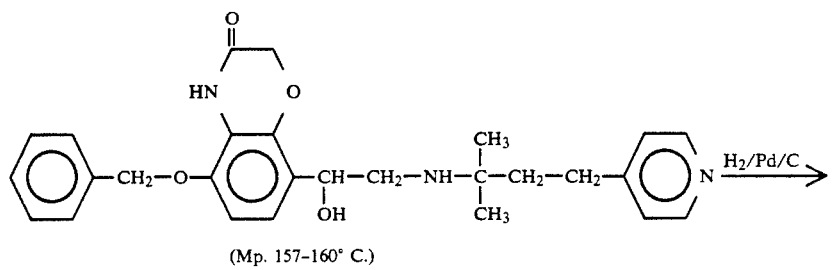

(Mp. 157–160° C.)

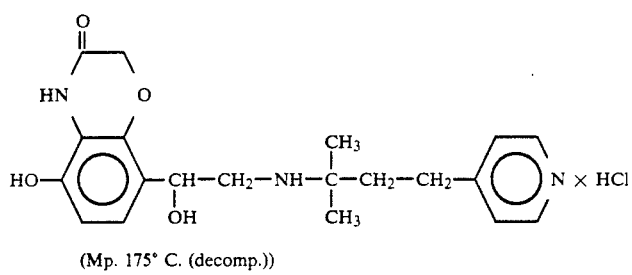

(Mp. 175° C. (decomp.))

EXAMPLE 2

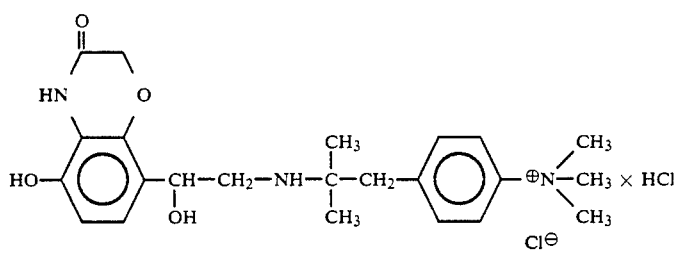

3.7 g of 5'-benzyloxy-8'-[1-hydroxy-2-[3-(4-dimethylaminophenyl)-2-methyl-2-propylamino]-ethyl]-2H-1,4-benzoxazin-3-(4H)-one-monohydrochloride are combined with 2.1 g of methyliodide in 7.4 ml of DMF and reacted for 12 hours. After dilution of the solution with acetone the ammonium iodide hydrochloride is obtained which is converted into the ammonium chlorohydrochloride compound (m.p. 195°–197° C.) by conversion with hydrochloric acid or by means of the ammonium hydroxide compound and treating with hydrochloric acid.

3.7 g of this benzyloxy compound are debenzylated in 50 ml of methanol using palladium/charcoal as catalyst under normal conditions and 2 g of the title compound are obtained. M.p. 187° C. (decomp.); (6.28% of theory).

The starting compound may be prepared by the following method:

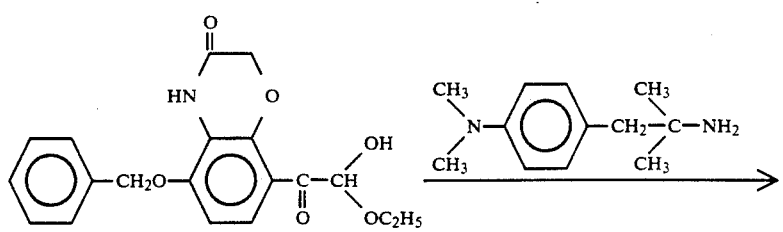

-continued

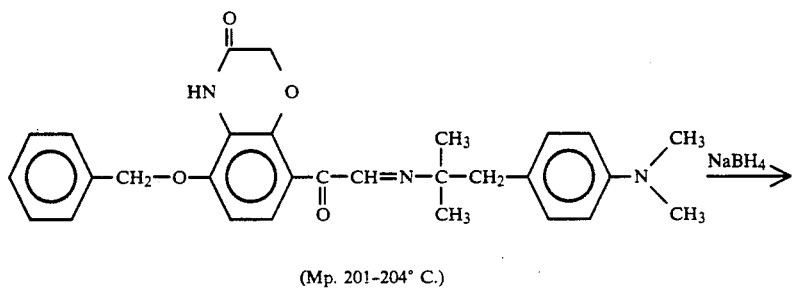

(Mp. 201-204° C.)

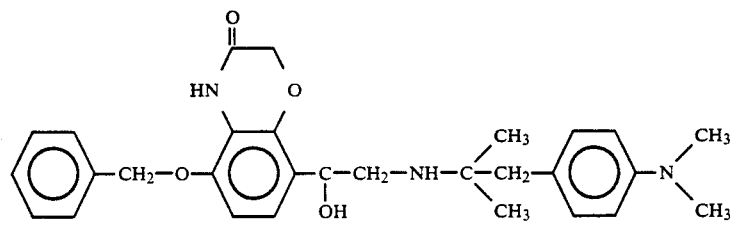

(Mp. 110-112° C., Mp. HCl salt 232-235° C.)

EXAMPLE 3

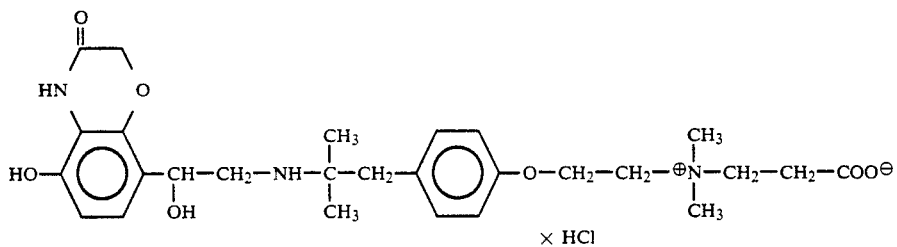

3.2 g of 5'-benzyloxy-8'-[1-hydroxy-2-[3-(4-dimethylamino-ethoxyphenyl)-2-methyl-2-propylamino]-ethyl]-2H-1,4-benzoxazin-2-(4H)-one-monohydrochloride are combined with 0.41 g of β-propiolactone in 6 ml of acetone and left to react for 12 hours at ambient temperature. After dilution with acetone, the crystals precipitated are suction filtered and 2.4 g of the compound are obtained (Mp. 123°-126° C.).

2.3 g of the benzyloxy compound are debenzylated in 50 ml of methanol with the addition of palladium charcoal and 1.7 g of the title compound are obtained. (Mp. 173°-175° C., 94% of theory).

The starting compound may be prepared by the following method:

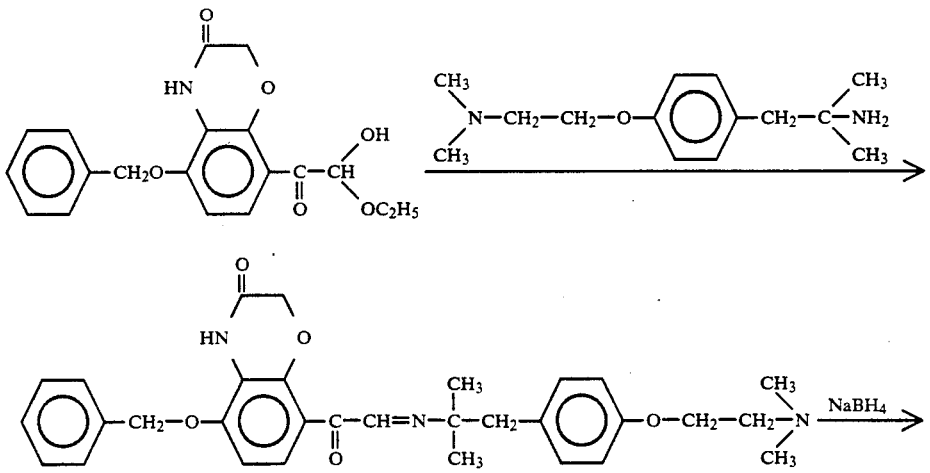

(Mp. 153-155° C.)

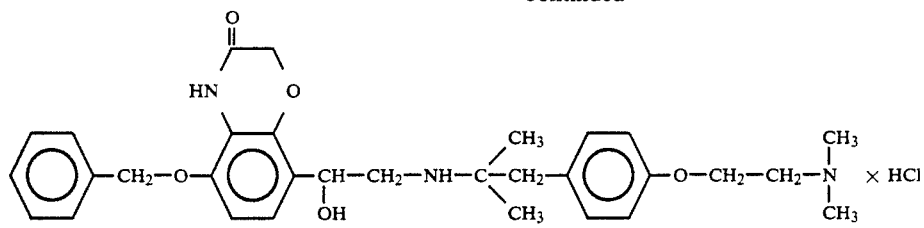
(Mp. 176–178° C.)
The following compounds may be synthesised analogously to the Examples given:
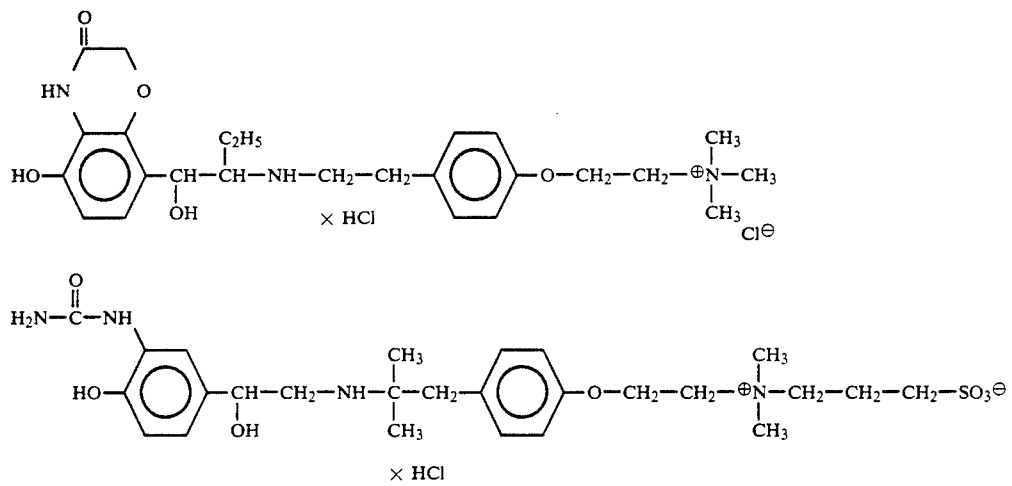
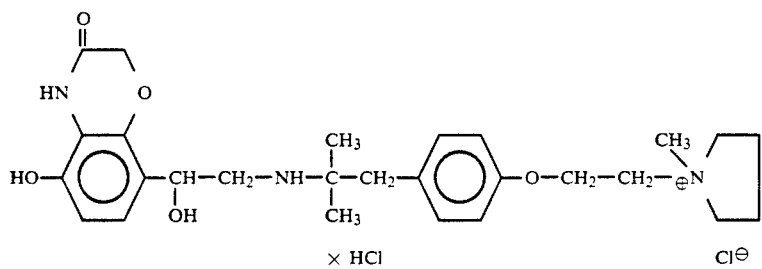
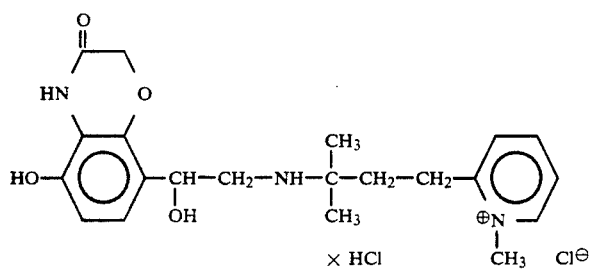
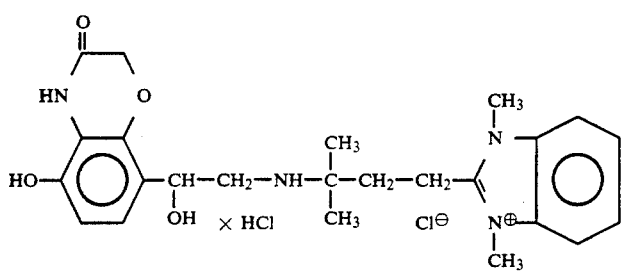

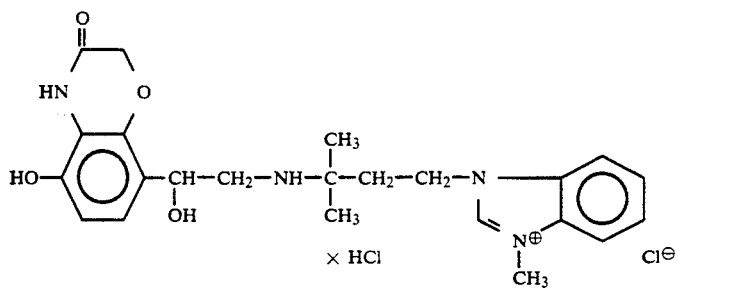
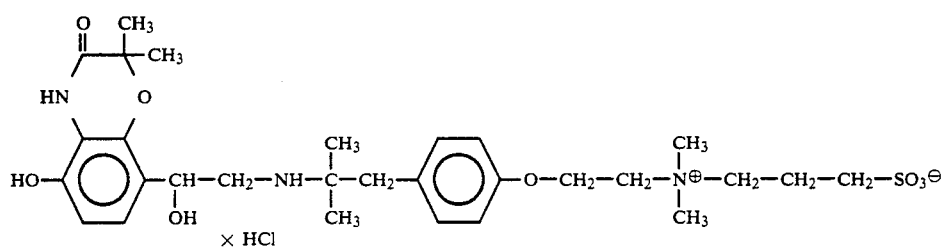
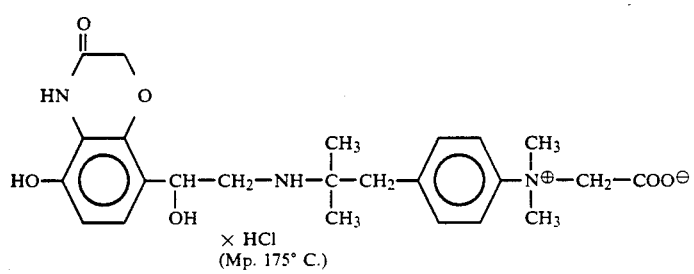
(Mp. 175° C.)
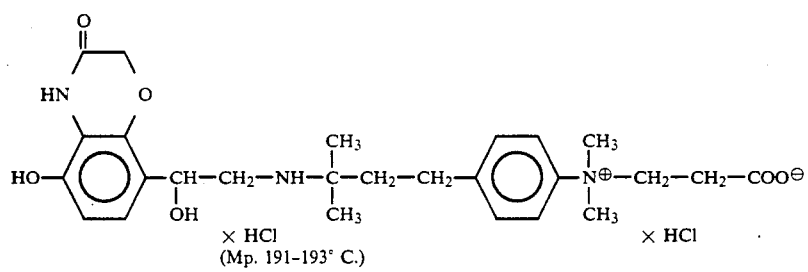
(Mp. 191–193° C.)
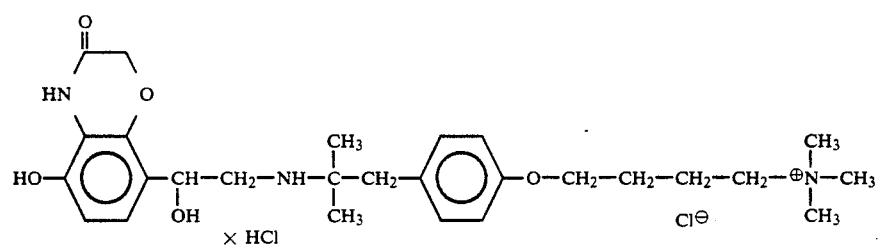
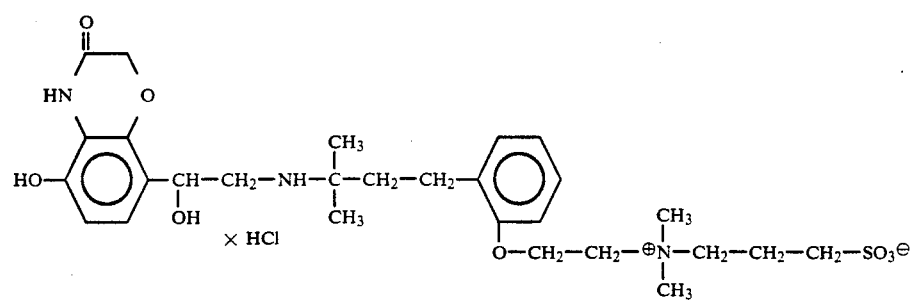

-continued
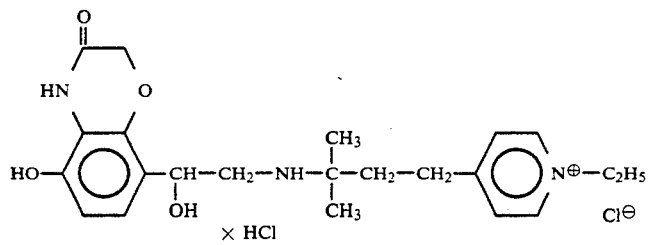
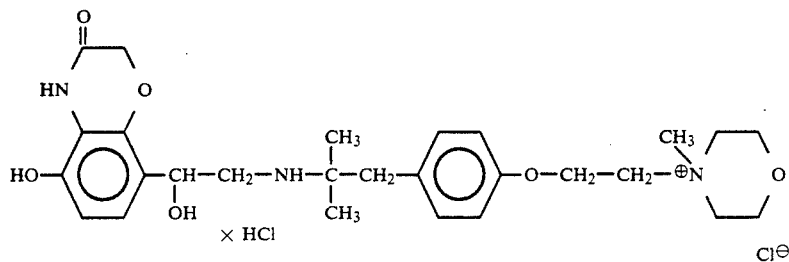
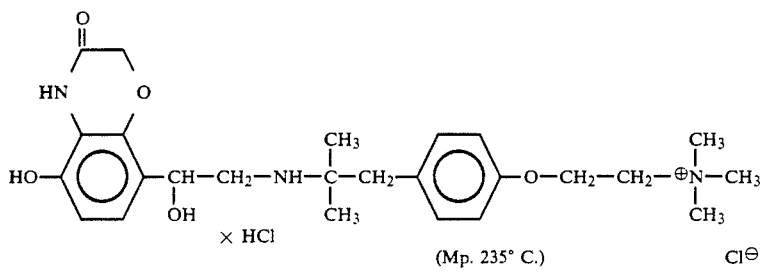
(Mp. 235° C.)
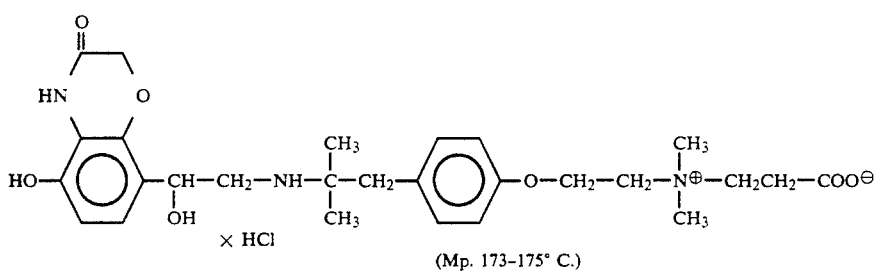
(Mp. 173–175° C.)
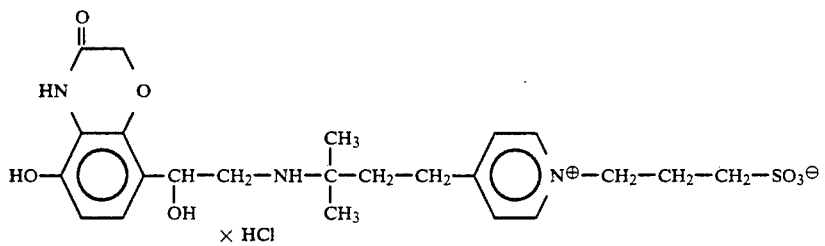
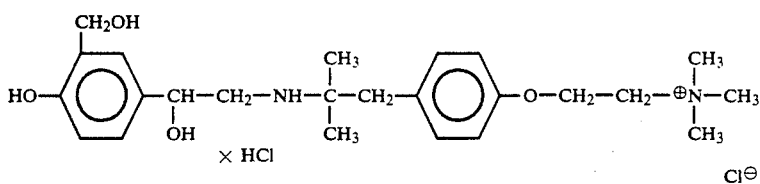

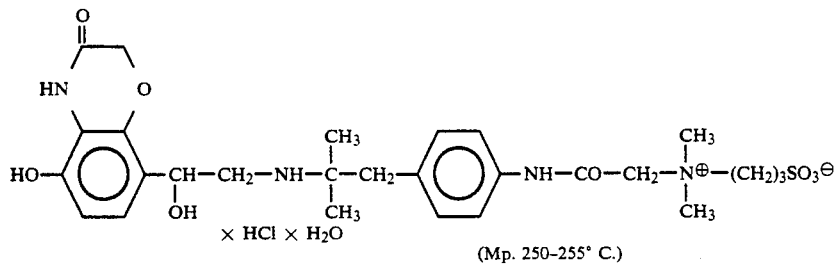
(Mp. 250–255° C.)
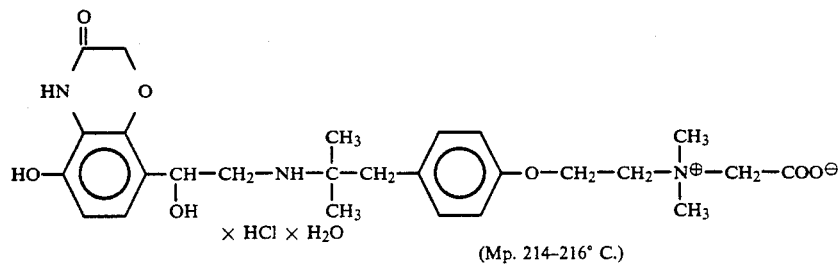
(Mp. 214–216° C.)
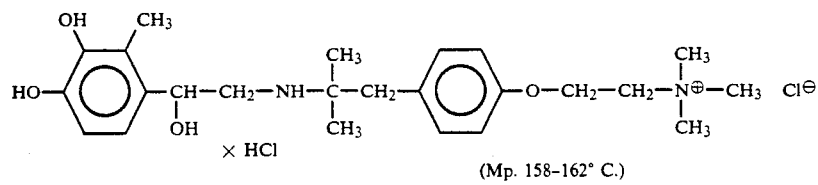
(Mp. 158–162° C.)
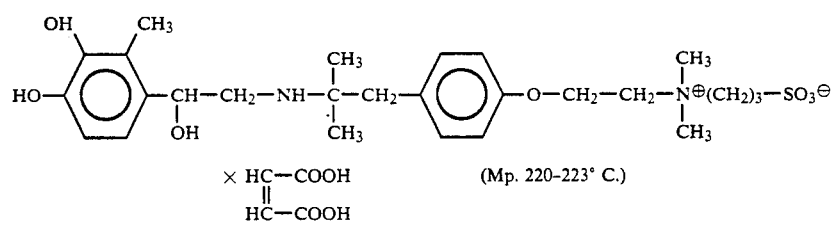
(Mp. 220–223° C.)
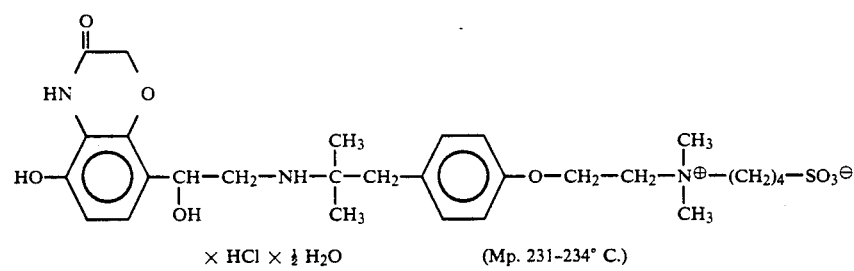
(Mp. 231–234° C.)
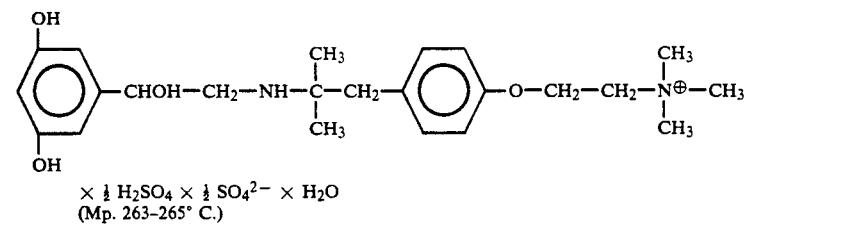
(Mp. 263–265° C.)
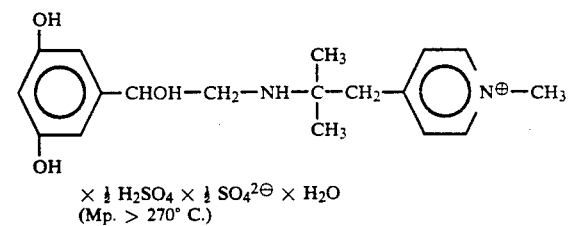
(Mp. > 270° C.)

-continued

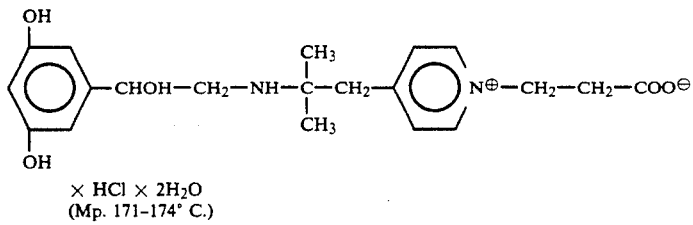
× HCl × 2H₂O
(Mp. 171-174° C.)

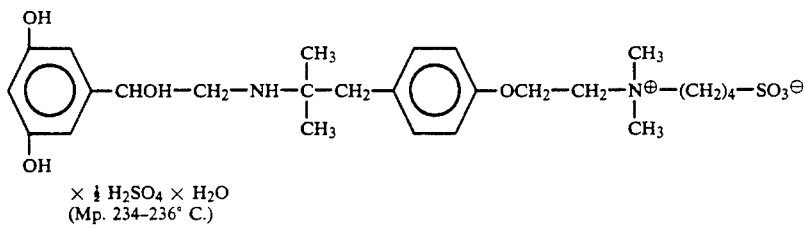
× ½ H₂SO₄ × H₂O
(Mp. 234-236° C.)

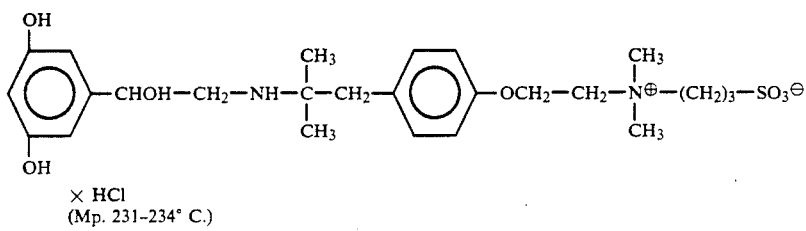
× HCl
(Mp. 231-234° C.)

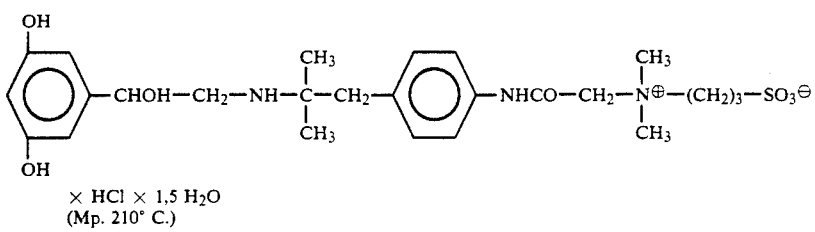
× HCl × 1,5 H₂O
(Mp. 210° C.)

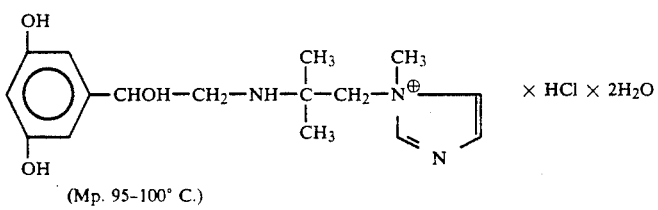
(Mp. 95-100° C.)

EXAMPLE 4

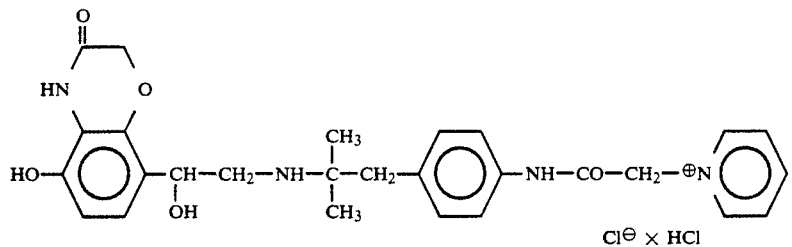

4.4 g of 5′-hydroxy-8′-[1-hydroxy-2-[3-(4-chloroacetaminophenyl)-2-methyl-2-propylamino]-ethyl]-2H-1,4-benzoxazin-3-(4H)-one-hydrochloride, 6 ml of pyridine and 25 ml of methanol are refluxed for 6 hours, then after the methanol and pyridine have been distilled off the oily residue is dissolved in alcohol and 3.8 g of the title compound are obtained.

(Mp. 190°-192° C.; 77.5% of theory).

The starting compound may be prepared by the following processes:

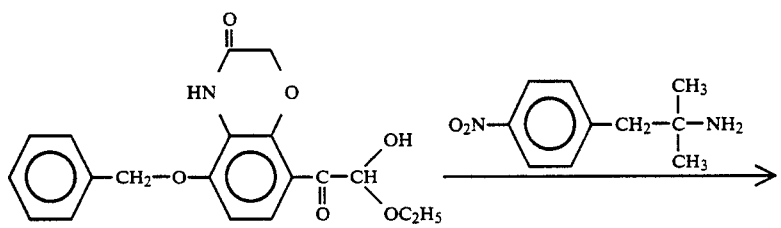
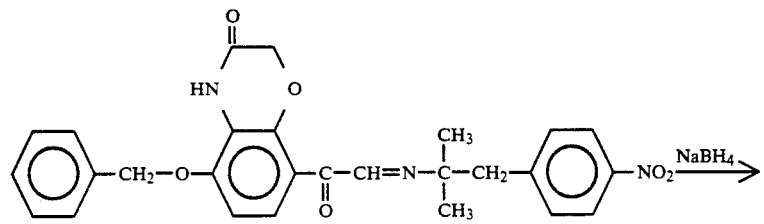
(Mp. 151-154° C.)
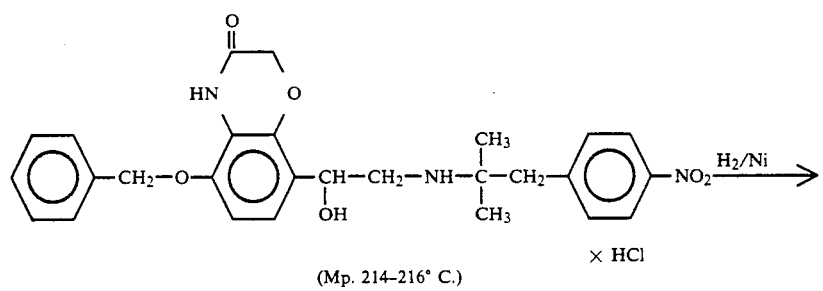
(Mp. 214-216° C.)
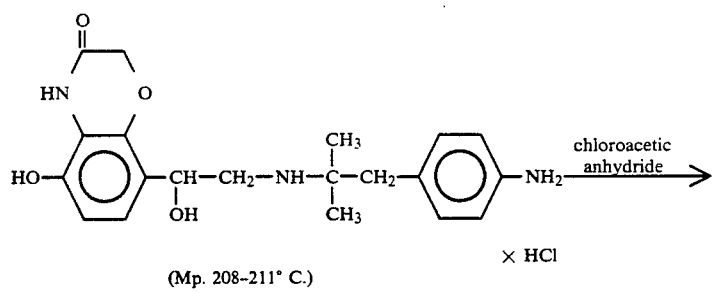
(Mp. 208-211° C.)
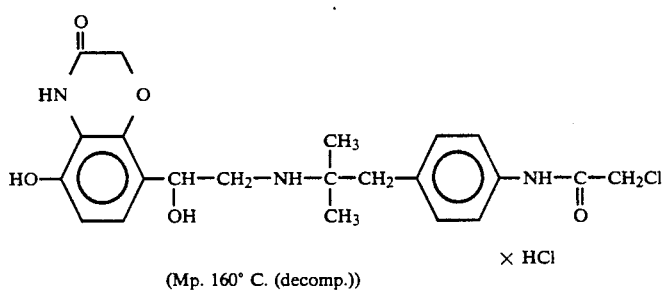
(Mp. 160° C. (decomp.))

EXAMPLE 5

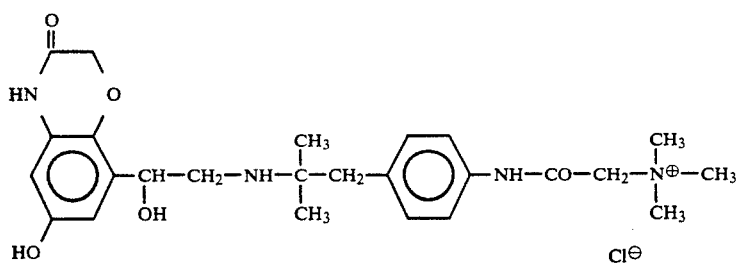

2.7 g of 6'-hydroxy-8'-[1-hydroxy-2-[3-(4-chloracetaminophenyl)-2-methyl-2-propylamino]-ethyl]-2H-1,4-benzoxazin-3-(4H)-one-hydrochloride, 25 ml of methanol and 3 ml of 30% trimethylamine solution are stirred for 12 hours at ambient temperature, concentrated and the oil obtained is dissolved in alcohol. After 1 hour the crystals precipitated are suction filtered and 2 g of the title compound are obtained. (Mp. 203°–206° C., 65% of theory)

The starting compound may be prepared by the following process:

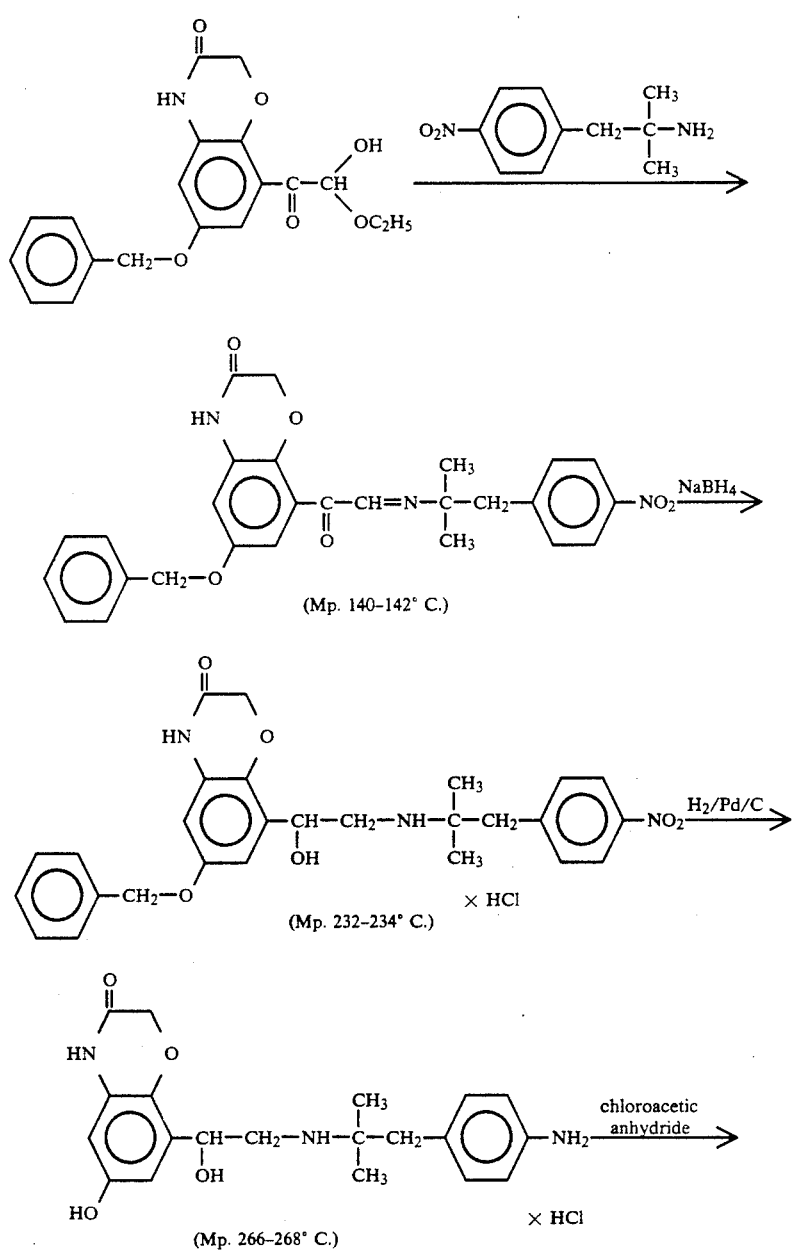

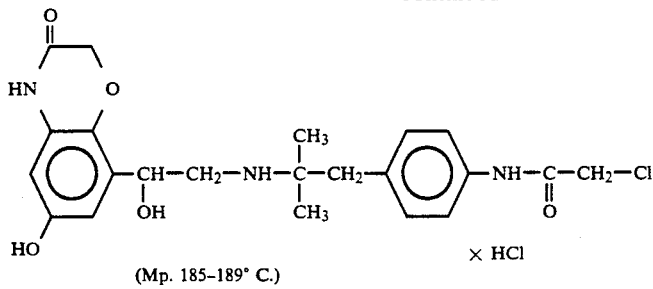
(Mp. 185–189° C.)
The following compounds are prepared analogously:
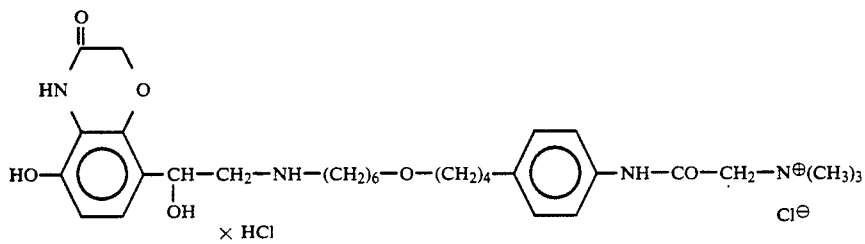
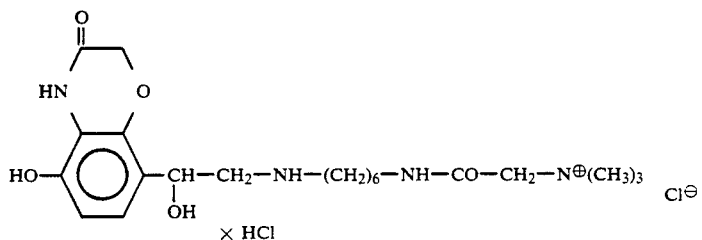
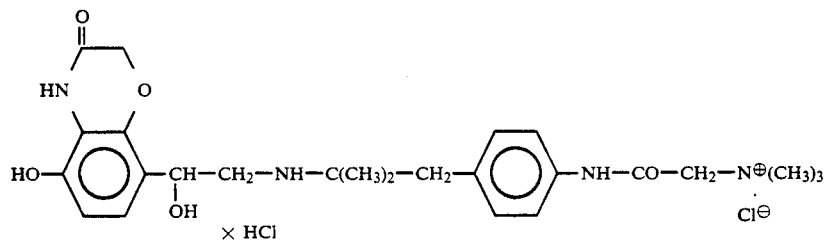
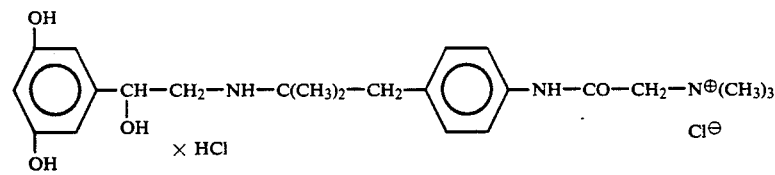
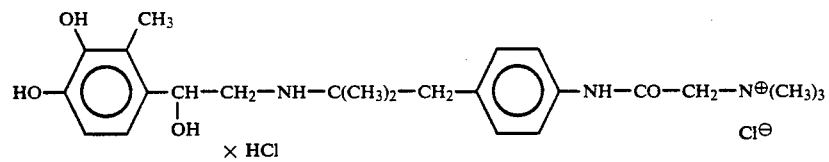
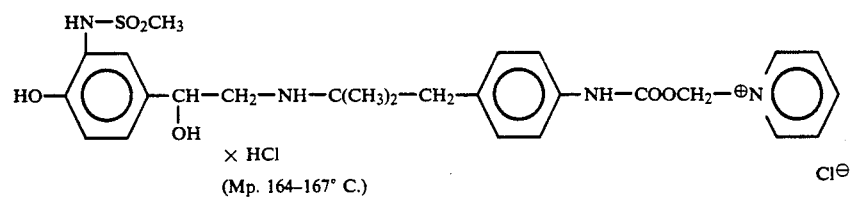
(Mp. 164–167° C.)

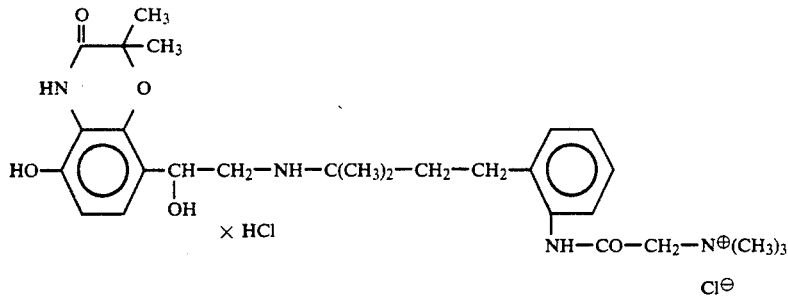

EXAMPLE 6

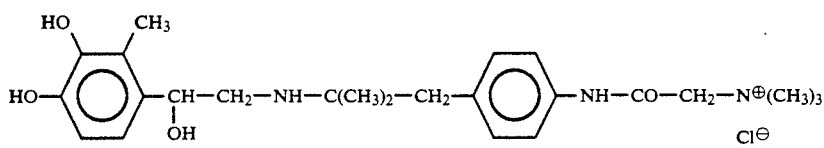

4.2 g of dibenzyloxy compound (see below) are debenzylated with hydrogen in methanol with palladium charcoal as catalyst under normal conditions and 2.5 g of the title compound are obtained. (81% of theory).

The starting compound may be prepared by the following method:

addition of 0.5 g of 5% palladium charcoal as catalyst under normal conditions. After the uptake has ceased the catalyst is removed by suction filtering, the methanol is distilled off under reduced pressure using a Rotavapor and the residue is dissolved in approximately 90% alcohol. After seeding the crystals precipitated are suction filtered, washed with alcohol and dried. 2.9 g of the title compound are obtained, (Mp. 240° C.; 93% of theory).

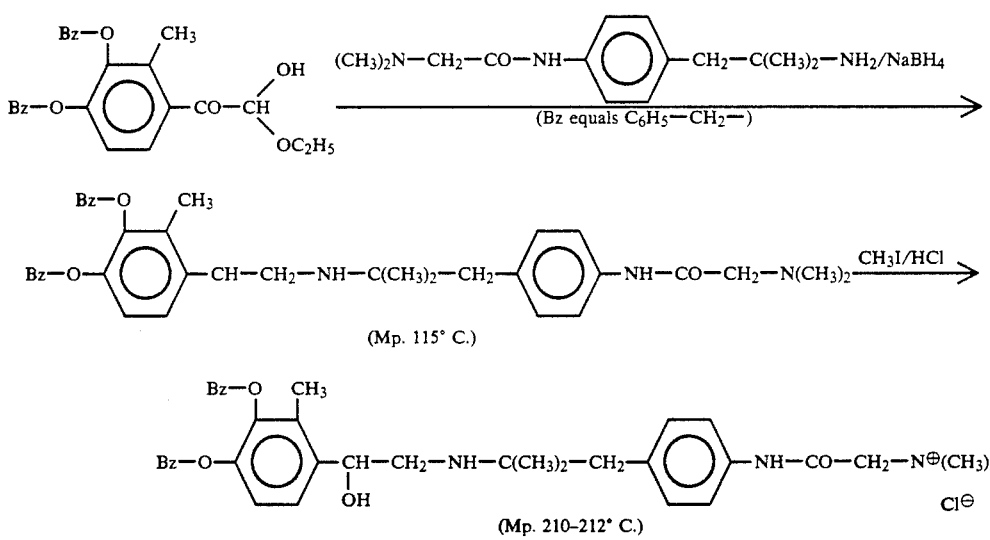

EXAMPLE 7

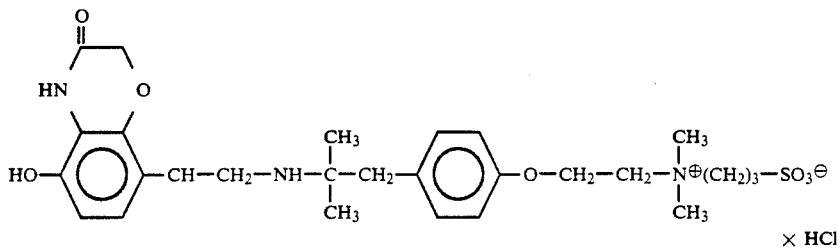

3.5 g of benzoyloxy compound (see below) are debenzylated with hydrogen in 50 ml of methanol with the The starting compound may be prepared by the following process (Bz equals benzyl)

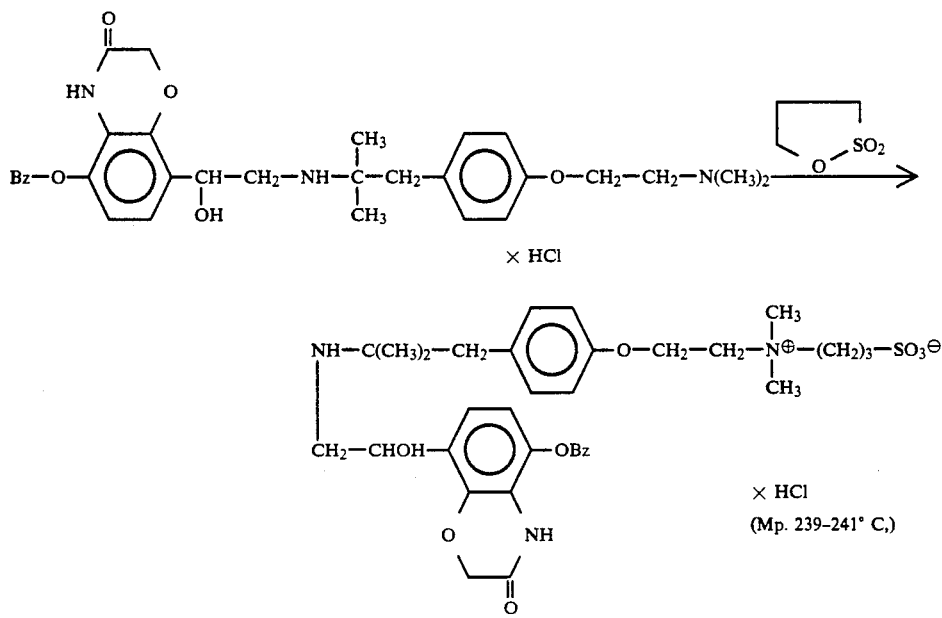

EXAMPLE 8

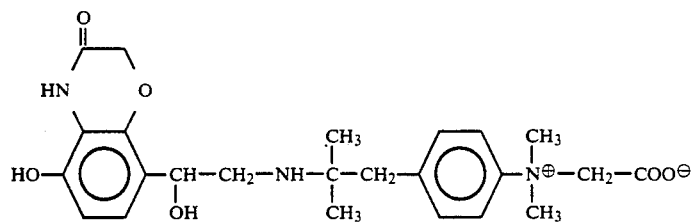

2.4 g of benzyloxy compound are debenzylated with hydrogen in 50 ml of methanol and 10 ml of water with the addition of 0.5 g of palladium/charcoal as catalyst under normal conditions. After the uptake has ceased the catalyst is removed by suction filtering, the methanol is distilled off under reduced pressure using a Rotavapor and the residue is triturated with alcohol. The crystals precipitated are suction filtered and reprecipitated once with water/alcohol. 1.6 g of the title compound are obtained, (mp. 175° C., decomp., 71% of theory)

The starting compounds may be obtained by the following process:

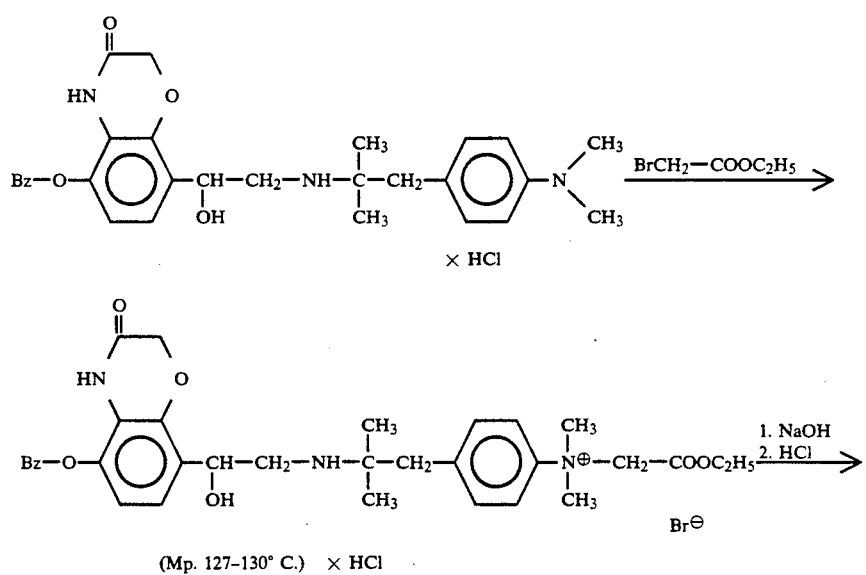

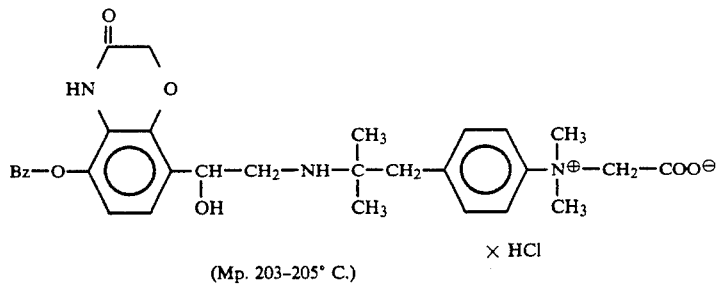
(Mp. 203–205° C.)
The following compounds may be synthesised analogously to the Examples:
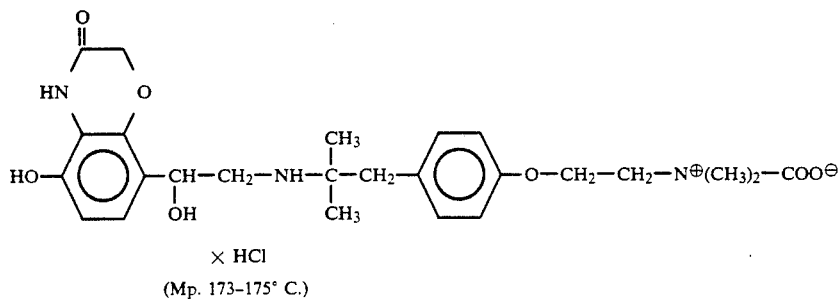
× HCl
(Mp. 173–175° C.)
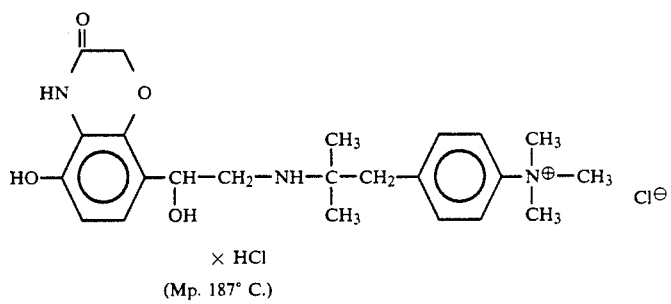
× HCl
(Mp. 187° C.)
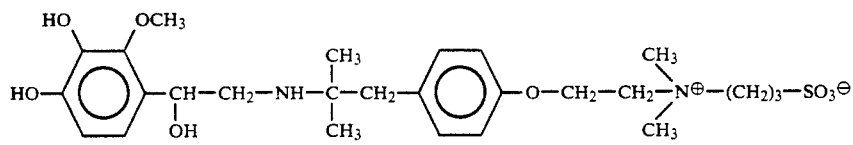
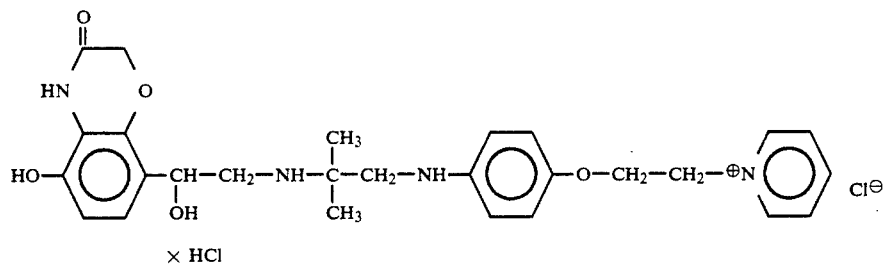
× HCl
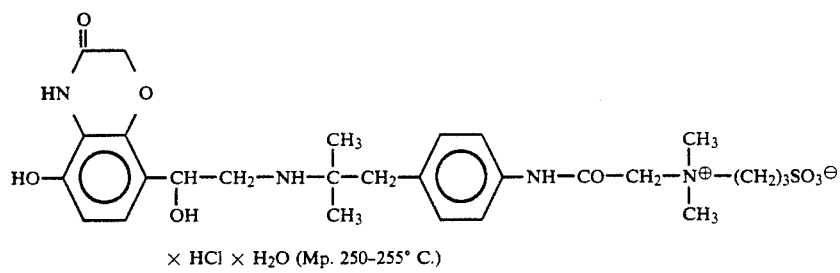
× HCl × H₂O (Mp. 250–255° C.)

-continued
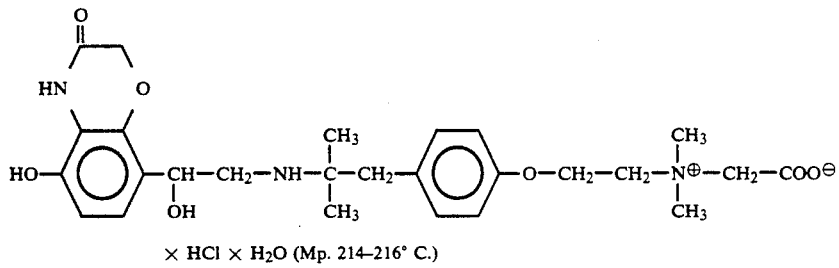
× HCl × H₂O (Mp. 214–216° C.)
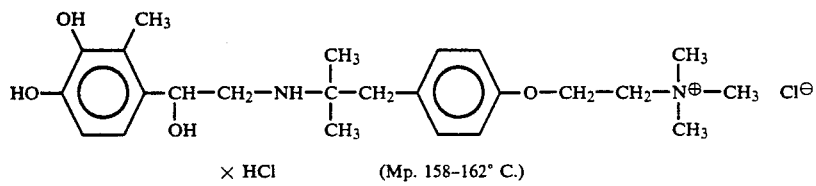
× HCl    (Mp. 158–162° C.)
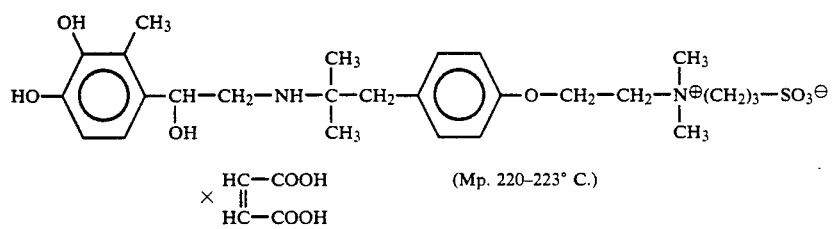
(Mp. 220–223° C.)
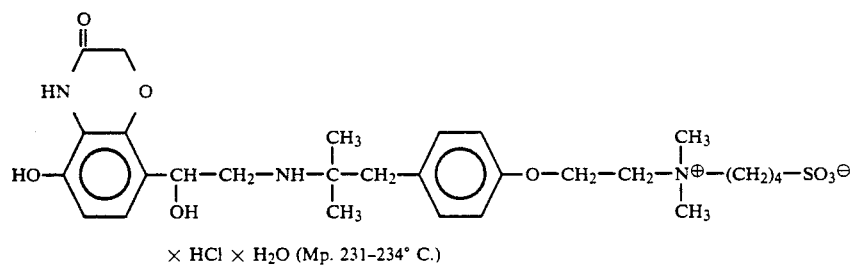
× HCl × H₂O (Mp. 231–234° C.)
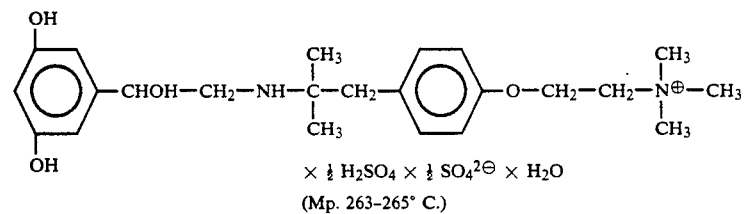
× ½ H₂SO₄ × ½ SO₄²⁻ × H₂O
(Mp. 263–265° C.)
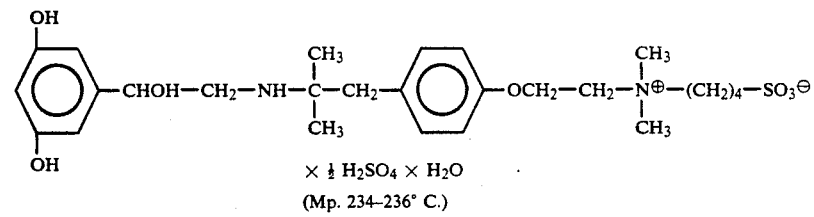
× ½ H₂SO₄ × H₂O
(Mp. 234–236° C.)
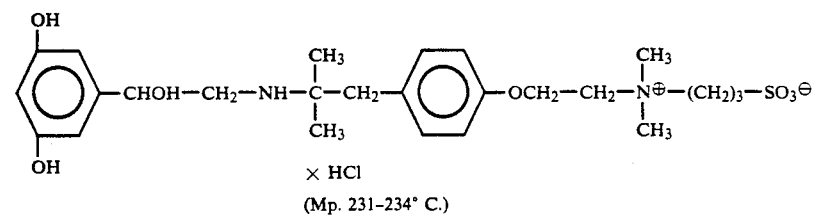
× HCl
(Mp. 231–234° C.)

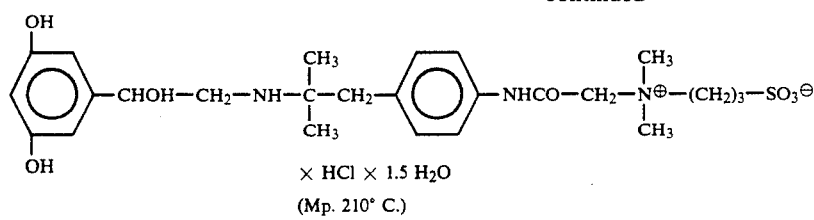

× HCl × 1.5 H$_2$O
(Mp. 210° C.)

What is claimed is:

1. A compound of formula

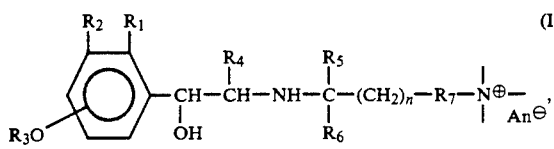 (Ia)

wherein n is an integer 1, 2, 3, 4 or 5;

R$_1$ is H, CH$_3$, OCH$_3$, Cl or F;

R$_2$ is H, R$_3$O, CH$_2$OH, NHCHO, NHCOCH$_3$, NHSO$_2$CH$_3$, or NHCONH$_2$;

R$_3$ is H, acyl, N,N-dialkylcarbamoyl, the group R$_3$O being in the 4 or 5 position; or the group

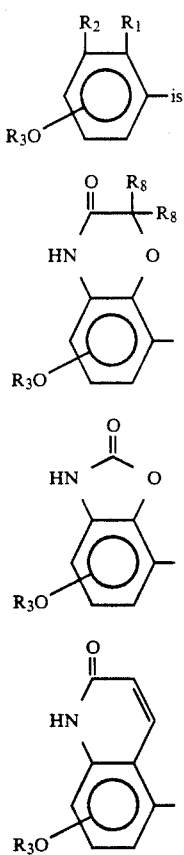

wherein R$_3$ is as defined above and R$_8$ is H or CH$_3$;

R$_4$ is H, CH$_3$, or C$_2$H$_5$;

R$_5$ is H or CH$_3$;

R$_6$ is H or CH$_3$;

R$_7$ is a single bond or a divalent bridging member which may also be bound to the ammonium nitrogen via ring atoms of a heterocyclic group;

R$_8$ is H, or —CH$_3$;

is a quaternary ammonium group,

An$^-$ is 1 equivalent of an anion, a pure enantiomer thereof, or a mixture of enantiomers, or a salt with inorganic or organic acids.

2. The compounds as recited in claim 1, wherein the group

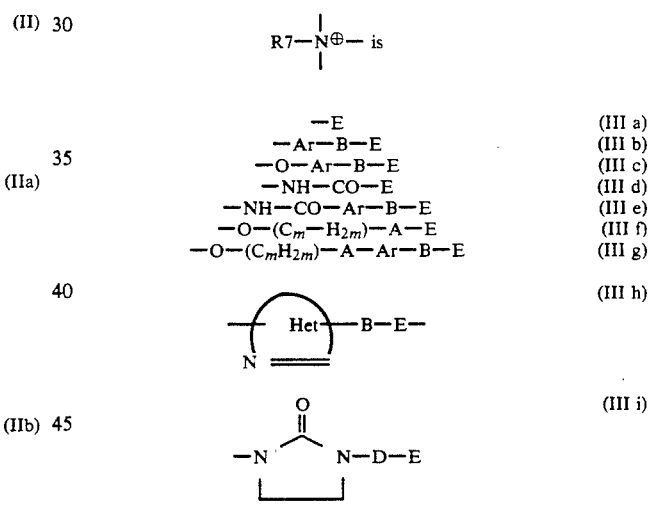

| | |
|---|---|
| —E | (III a) |
| —Ar—B—E | (III b) |
| —O—Ar—B—E | (III c) |
| —NH—CO—E | (III d) |
| —NH—CO—Ar—B—E | (III e) |
| —O—(C$_m$—H$_{2m}$)—A—E | (III f) |
| —O—(C$_m$H$_{2m}$)—A—Ar—B—E | (III g) | wherein n and R$_1$ to R$_6$ are as recited in claim 2 and m is an integer 2, 3, 4, 5 or 6;

A is a single bond or NH—CO—(C$_{1-4}$)-alkylene;

B is a single bond, —O—(C$_{1-4}$)-alkylene, —(C$_{1-4}$)-alkylene, or —NH—CO—(C$_{1-4}$)-alkylene;

D is —(C$_{1-4}$)-alkylene

E is

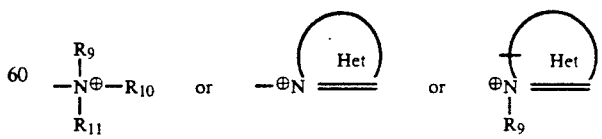

wherein

R9 is (C$_{1-4}$)-alkyl;

R10 is (C$_{1-4}$)-alkyl;

$R_{11}$ is $(C_{1-4})$-alkyl, $(C_{1-4})$-alkylene-COO—$(C_{1-4})$-alkylene-SO$_3$—, $(C_{1-4})$-alkylene-OH, $(C_{1-4})$-cycloalkyl, $R_9$ and $R_{10}$ together are $(C_{4-6})$-alkylene.

Ar is arylene, and

is N-heterocycles which may be condensed with a benzene ring and may be substituted or unsubstituted and may optionally contain one or more additional heteroatoms in the ring.

3. The compound as recited in claim 2 wherein Ar is unsubstituted or substituted phenylene or naphthylene.

4. A pharmaceutical composition of matter useful in the treatment of bronchospasm comprising a therapeutically effective amount of a compound as recited in claim 2 and a pharmaceutically acceptable carrier.

5. A method of treating bronchospasm in a warm-blooded animal comprising administering to said animal a therapeutically effective amount of a compound as recited in claim 1.

* * * * *